United States Patent [19]

Kabbe et al.

[11] Patent Number: 5,221,681
[45] Date of Patent: Jun. 22, 1993

[54] SUBSTITUTED BENZOXAZEPINES AND BENZOTHIAZEPINES

[75] Inventors: Hans-Joachim Kabbe; Helmut Heitzer, both of Leverkusen; Andreas Knorr, Erkrath; Claudia Hirth-Dietrich, Wuppertal, all of Fed. Rep. of Germany

[73] Assignee: Bayer Aktiengesellschaft, Leverkusen, Fed. Rep. of Germany

[21] Appl. No.: 823,108

[22] Filed: Jan. 16, 1992

[30] Foreign Application Priority Data

Jan. 25, 1991 [DE] Fed. Rep. of Germany ....... 4102103

[51] Int. Cl.$^5$ ................... A61K 31/40; A61K 31/44; C07D 491/08; C07D 495/08
[52] U.S. Cl. .................................. 514/338; 514/411; 546/270; 548/421; 548/430; 549/23; 549/396
[58] Field of Search ..................... 546/270; 548/430; 514/338, 411; 540/552

[56] References Cited

FOREIGN PATENT DOCUMENTS 0415065 3/1991 European Pat. Off. .
2194786 3/1988 United Kingdom .

OTHER PUBLICATIONS

Hans-Joachim Kabbe, "4-Acyl-2,3,4,5-tetrahydro-2-methyl 2,5-methanobenz-1,4-oxazepine, Derivatives of a New Heterocycle," Angewandte Chemie International Edition, 30(12), (1991), pp. 1709-1711.

*Primary Examiner*—Mukund J. Shah
*Assistant Examiner*—Philip I. Datlow
*Attorney, Agent, or Firm*—Sprung Horn Kramer & Woods

[57] ABSTRACT

The present invention relates to new substituted benzoxazepines and benzothiazepines of the general formula I

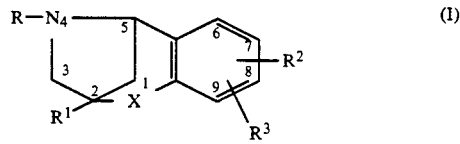

in which X, $R^1$, $R^2$ and $R^3$ have the meaning given in the description, processes for their preparation and their use in medicaments having vaso- and muscle-relaxing properties, in particular as circulatory agents.

5 Claims, No Drawings

SUBSTITUTED BENZOXAZEPINES AND BENZOTHIAZEPINES

The present invention relates to new substituted benzoxazepines and benzothiazepines, processes for their preparation and their use in medicaments having vaso- and muscle-relaxing properties, in particular as circulatory agents.

Active compounds having vaso- and muscle-relaxing actions, some of which are also employed as circulatory agents, are already known (compare European Patent 0,388,528). However, the compounds from the prior art clearly differ from the compounds according to the invention both in their chemical structure and in their action profile.

The invention relates to new 2,5-methano-benzoxazepines and -benzothiazepines of the general formula (I)

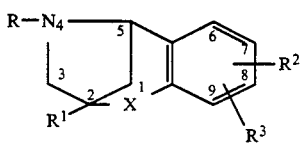

in which

X represents oxygen or sulphur,

R represents hydrogen or one of the groups $COR^4$, $CO-NHR^4$, $CS-NHR^4$, $CO-OR^4$ or $SO_2R^4$, wherein $R^4$ in each case represents hydrogen, straight-chain, branched or cyclic alkyl having up to 7 C atoms, alkenyl having 2 to 4 C atoms, phenalkyl having 7 to 10 C atoms, phenyl or a 5- or 6-membered heteroaryl radical which contains one or two identical or different hetero atoms from the group comprising oxygen, sulphur and nitrogen, it being possible for the alkyl radicals mentioned to be optionally substituted by halogen and for the phenyl radicals to be optionally mono- or disubstituted by alkyl or alkoxy having in each case 1 to 4 C atoms or by halogen or nitro, $R^1$ represents hydrogen or alkyl having 1 to 4 C atoms and $R^2$ and $R^3$ are identical or different and in each case represent one or two substituents from the group comprising hydrogen straight-chain, branched or cyclic alkyl having 1 to 7 C atoms, which is optionally substituted by halogen, alkoxy having 1 to 6 C atoms, halogen, nitro, carboxyl, hydroxyl, carboxamide, alkoxycarbonyl having up to 7 C atoms, alkylsulphonyl having 1 to 6 C atoms, phenylsulphonyl and a 5- or 6-membered heteroaryl radical which contains one or two hetero atoms from the group comprising nitrogen, oxygen and sulphur, or represent phenyl which is optionally mono- or disubstituted by alkyl or alkoxy having 1 to 4 C atoms, halogen or nitro, or represent $COR^4$, or $R^2$, together with $R^3$, forms a 3- or 4-membered fused-on ring, both in the form of isomer mixtures and in isomerically pure form.

The compounds according to the invention lower the cation content in muscle and vessel cells. In particular, they have a positive influence on calcium ions and potassium ions. The compounds according to the invention preferably have a relaxing action on blood vessels and bronchi and can therefore be used for the treatment of circulatory diseases, in particular hypertension and asthma.

Compounds which are of particular importance are those of the general formula (I) in which X represents oxygen or sulphur, R represents hydrogen, $COR^4$, $CONHR^4$, $CSNHR^4$, $COOR^4$ or $SO_2R^4$, wherein $R^4$ represents alkyl or alkoxy having up to 4 C atoms, it being possible for alkyl to be optionally substituted by fluorine or chlorine, or represents phenyl which is optionally mono- or disubstituted by alkyl or alkoxy having 1 to 4 C atoms, fluorine, chlorine or nitro, or represents heteroaryl from the group comprising thiophene, pyridine or furan, which are optionally substituted by fluorine, chlorine, methyl, ethyl or methoxy, $R^1$ represents hydrogen or alkyl having 1 to 4 C atoms and $R^2$ and $R^3$ are identical or different and in each case represent one or two substituents from the group comprising hydrogen, halogen, nitro, carboxyl, cyano, hydroxyl, carboxamide, phenyl, phenylsulphonyl, alkyl having 1 to 4 C atoms, alkoxy having 1 to 4 C atoms, alkoxycarbonyl having up to 5 C atoms, alkylsulphonyl having 1 to 4 C atoms, thiophene, pyridine and furan, the alkyl, aryl and heteroaryl radicals mentioned optionally being substituted by fluorine, chlorine, nitro, alkyl having 1 to 4 C atoms or alkoxy having 1 to 4 C atoms, or $R^2$ and $R^3$ together form a 3- or 4-membered fused-on ring.

Compounds which are particularly preferred are those of the general formula (I) in which X represents oxygen, R represents hydrogen, $CO-R^4$, $CO-NH-R^4$, $COOR^4$ or $SO_2-R^4$, wherein $R^4$ represents alkyl or alkoxy having 1 to 4 C atoms, it being possible for alkyl to be substituted by fluorine, $R^1$ represents alkyl having 1 to 4 C atoms and $R^2$ and $R^3$ are identical or different and in each case represent 1 or 2 substituents from the group comprising hydrogen, halogen, nitro, cyano, alkyl having up to 4 C atoms and alkylsulphonyl having up to 4 C atoms, it being possible for the alkyl radicals mentioned to be substituted by fluorine.

The compounds of the general formula (I) according to the invention can be prepared by a process in which compounds of the general formula (II)

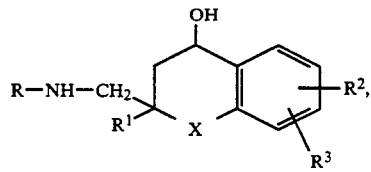

in which X, R, $R^1$, $R^2$ and $R^3$ have the abovementioned meaning, are subjected to condensation at temperatures between 60° and 200° C., preferably between 70° and 140° C., in inert organic solvents in the presence of acids, the water formed being distilled off azeotropically if appropriate.

Acids which are used are preferably high-boiling anhydrous acids, such as sulphuric acid, alkyl-, aralkyl- or arylsulphonic acids having up to 10 C atoms or phosphoric acid.

The organic solvents used are preferably those which are inert towards the reaction partners and which boil at the reaction temperature and can thus remove the water azeotropically, such as, for example, hydrocarbons, such as cyclohexane, petroleum ether, benzene, toluene or xylene, halogenohydrocarbons, such as chlorobenzene or dichlorobenzene, esters, such as butyl acetate, or mixtures of the solvents mentioned.

The starting compounds of the formula (II) are prepared by customary methods, for example by cyclisation of o-hydroxyacetophenone derivatives of the general formula (III)

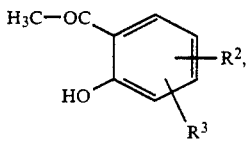

with ketones of the general formula (IV)

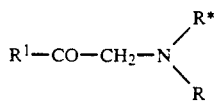

in which
R* represents hydrogen or an acyl radical which can be split off, as defined under R,
to give benzopyranones of the formula (V)

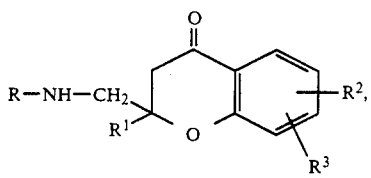

wherein
R, $R^1$, $R^2$ and $R^3$ have the abovementioned meaning, by methods which are known per se (for example H. J. Kabbe et al., Ang. Ch. 94, 254 (1982)) and by subsequent reduction of the compounds (V) by customary methods, for example with complex hydrides, such as, for example, sodium borohydride, in inert solvents, such as alcohols, or by catalytic hydrogenation in the presence of heavy metal catalysts.

The compounds according to the invention display an unforeseeable useful pharmacological action spectrum. They can therefore be employed for the preparation of medicaments for the treatment of circulatory diseases, in particular hypertension, or for the treatment of salt balance diseases or of spasms, or for the treatment of asthma.

Their interesting actions can be demonstrated by the following pharmacological test:

The compounds according to the invention have a powerful and persistent antihypertensive action on rats with spontaneous hypertension.

This action was found on conscious animals whose blood pressure was measured by the indirect tail microphone technique before and 1, 2, 4, 6 and 24 hours after oral administration.

A powerful reduction in blood pressure which persisted for several hours was thus observed after doses of only about 5 mg/kg (Example 5).

The new active compounds can be converted into the customary formulations, such as tablets, coated tablets, pills, granules, syrups, aerosols, emulsions, suspensions and solutions, in a known manner. Inert, non-toxic, pharmaceutically suitable excipients or auxiliaries are employed for this purpose.

Embodiment Examples

Example I 20.2 g (0.2 mol) of formylaminoacetone [A. Treibs u.a., Chem. Ber. 84 96 (1951)] and 27.2 g (0.2 mol) of o-hydroxyacetophenone are dissolved in 100 ml of toluene, and 10 ml of pyrrolidine are added. The mixture is stirred at 25° C. for 20 hours and then at 115° C. for 2 hours. After cooling, the mixture is extracted by shaking successively with 2N HCl, 2N NaOH and water, the organic phase is concentrated and the 2-methyl-2-formylaminomethylchroman-4-one formed is isolated by chromatography. Melting point: 96°–8° C.

Example II 142 g (0.87 mol) of diacetylamino-acetone and 120 g (0.88 mol) of o-hydroxyacetophenone are dissolved in 400 ml of toluene and, after addition of 185 ml of pyrrolidine, the mixture is stirred at 25° C. for 4 days. After the same working up as in Example 1, a toluene solution is obtained, which is concentrated. After addition of ether, 67.8 g of 2-methyl-2-acetylaminomethyl-chroman-4-one precipitate (melting point: 98°–100° C.). The combined aqueous extracts are extracted by shaking with n-butanol; the organic phase gives a further 69 g of the same chromanone after concentration and purification by chromatography. $^1$H-NMR(CDCl$_3$): 1.38 ppm (s,CH$_3$); 2.05 (s,CH$_3$CO); 2.75 (q,CH$_2$, $\delta_{AB}$=16.5 Hz); 3.58 (d/q, CH$_2$-NH, $\delta_{AB}$=14.0 Hz, $\delta_{ANH}$=5.5 Hz, $\delta_{BNH}$=7.0 Hz); 6.58 (d/d;NH); 6.9–7.9 (4 aromatic H).

Example III 60.9 g of the chromanone obtained in Example II are dissolved in 250 ml of methanol. 8 g of sodium borohydride are added at below 35° C., the mixture is stirred for 24 hours, NaBH$_4$ (8 g) is again added in portions and the mixture is subsequently stirred for a further 24 hours. The solution is concentrated. Water is added to the residue and the 2-methyl-2-acetylaminomethyl-chroman-4-ol formed is extracted with ether and butanol. Concentration of these extracts gives 55 g of end product of melting point 168°–70° C.

Example IV 20 g of the chromanone obtained in Example II are heated at the boiling point with 150 ml of 2N HCl for 5 hours. The solution is then brought to a pH of more than 12 with 2N NaOH and extracted with chlorobenzene. After concentration, 16.4 g of an oil remain, which is dissolved in 100 ml of toluene. 8 g of the mixed anhydride of acetic acid and formic acid are added, after which the temperature rises to 45° C. The mixture is subsequently heated at 60° C. for 8 hours and then concentrated. 13.5 g of 2-methyl-2-formylaminomethyl-chroman-4-one, which is identical to the product obtained in Example I, are obtained from the residue.

The following compounds are obtained analogously, in accordance with the experiments described above:

Example V

2-Methyl-2-acetylaminomethyl-6-chlorobenzopyran-4-one: melting point 111°-113° C.

Example VI

2-Methyl-2-acetylaminomethyl-7-methoxybenzopyran-4-one: melting point 145°-147° C.

Example VII

2-Methyl-2-acetylaminomethyl-6-trifluoromethoxybenzopyran-4-one, oily.

Example VIII

2-Methyl-2-benzoylaminomethylchroman-4-one: melting point 115°-117° C.

Example IX

2-Methyl-2-acetylaminomethyl-6-chlorochroman-4-ol: melting point 145°-147° C.

Example X

2-Methyl-2-benzoylaminomethylchroman-4-ol, oily isomer mixture.

Example 1

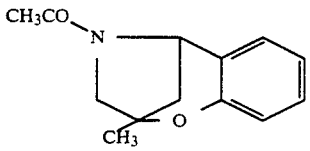

A mixture of 7.7 g of the chromanol obtained in Example III, 80 ml of chlorobenzene, 80 ml of cyclohexane and 0.5 g of p-toluenesulphonic acid is heated at the boiling point, using a water separator, a clear solution being formed. After 20 minutes, the solution is poured into an ice-cold sodium bicarbonate solution and the organic phase is washed with water, dried over $Na_2SO_4$ and concentrated to give 4.3 g of 2-methyl-4-acetyl-2,5-methano-2,3,4,5-tetrahydro-1,4-benzoxazepine. Melting point 110°-112° C. $^1$H-NMR(CDCl$_3$): 1.6 (s,CH$_3$ on C-2); 1.81 and 2.05 (2s,CH$_3$CO); 1.9-2.4 (2 overlapped ABX spectra, methanobridge); 3.4-3.8 (2 AB quartets, N—CH$_2$); 5.0-5 ppm (2d, H on C-5); 6.7-7.3 (m, 4 aromatic H).

Example 2

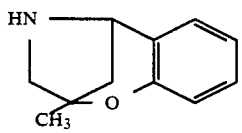

5 g of the benzoxazepine obtained in Example 1 are stirred in a mixture of 12 ml of 4N NaOH and 10 ml of glyme at the reflux temperature for 10 hours. After cooling, the end product formed is extracted with chlorobenzene. After the mixture has been concentrated, it is distilled. 2.7 g (67%) of 2-methyl-2,5-methano-2,3,4,5-tetrahydro-1,4-benzoxazepine are obtained (melting point 91°-3° C.). $^1$H-NMR (CDCl$_3$+CD$_3$OD); 1.62 (s,CH$_3$); 2.1 (CH$_2$,ABX, $\delta_{AB}$=11.4 Hz, $\delta_{AB}$=not resolved, $\delta_{BX}$=3.5 Hz); 3.2 (CH$_2$—NH,q, $\delta_{AB}$=12.0 Hz), 4.12 (CH,d,$\delta_{BX}$=3.5 Hz); 6.7-7.2 ppm (4 aromatic H).

Example 3

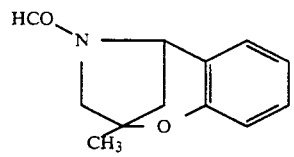

3.5 g of the amine obtained in Example 2 are dissolved in 8 ml of methylene chloride, and 2 ml of the mixed anhydride of formic acid and acetic acid are added. After 1 day, the mixture is concentrated, the residue is dissolved in a little ether, and petroleum ether is added until the solution becomes cloudy. After the mixture has been left to stand for one day, it is filtered with suction. 1.6 g of 2-methyl-4-formyl-2,5-methano-2,3,4,5-tetrahydro-1,4-benzoxazepine are obtained (melting point 103°-5° C.).

Example 4

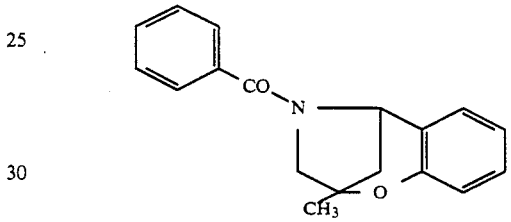

8.5 g of the amine obtained in Example 2 are dissolved in 30 ml of tetrahydrofuran and 7.3 ml of triethylamine. A solution of 6.8 g of benzoyl chloride in tetrahydrofuran is added dropwise (the temperature is kept below 30° C. by cooling with ice). After 5 hours, the mixture is poured into 300 ml of ice-water and the product is filtered off with suction and rinsed with ether.

Yield: 9.1 g (68%) of 2-methyl-4-benzoyl-2,5-methano-2,3,4,5-tetrahydro-1,4-benzoxazepine (melting point 48°-50° C.).

The same product is obtained if the chromanol obtained according to Example X is heated with p-toluenesulphonic acid in a mixture of chlorobenzene and cyclohexane (compare Example 1).

Example 5

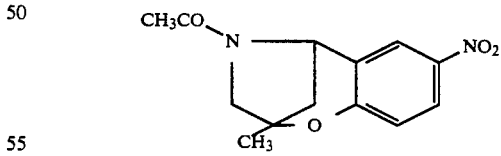

21.6 g of the product obtained in Example 1 are dissolved in 100 ml of acetic anhydride, the solution is heated to 50° C. and 30 g of copper(II) nitrate trihydrate are added in small portions at 50° to 55° C. in the course of 90 minutes. The mixture is subsequently stirred at the same temperature for a further 2 hours and is then poured into a mixture of ice-water and xylene. It is extracted twice with xylene, the extract is concentrated and the residue is dissolved in a little ether, after which the 2-methyl-4-acetyl-2,5-methano-2,3,4,5-tetrahydro-7-nitrobenzoxazepine formed precipitates. Yield: 17.1 g (66%); melting point 122°-124° C. $^1$H-NMR (CDCl$_3$):

1.60 (s,CH₃); 1.95 and 2.20 (s,CH₃—CO), 2.1–2.5 (CH₂, 2ABX multiplet); 3.6–3.9 (N-CH₂, 2AB multiplet); 4.99 and 5.32 (d,CH, δ=5.5 Hz); 6.8–8.2 (3 aromatic H).

Example 6

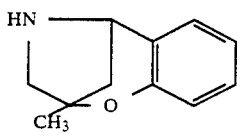

9.8 g of the compound obtained in Example 5 are heated under reflux in 100 ml of 2N HCl and 30 ml of glyme for 10 hours. After cooling, 3.8 g (41%) of 2-methyl-2,5-methano-2,3,4,5-tetrahydro-7-nitro-benzoxazepine are obtained as the hydrochloride (melting point 273°–276° C. decomposition). The mother liquor is brought to a pH of 12 with 2N NaOH. This mixture is extracted with ether, the extract is concentrated and the product is filtered off with suction; this gives 2.2 g (28%) of the above amine in the form of the free base (melting point 102°–104° C.).

Example 7

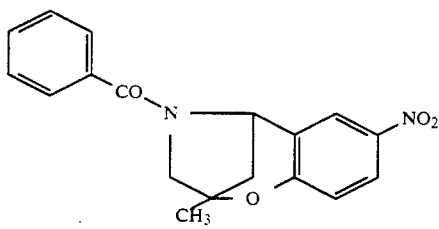

Acylation of the amine obtained in Example 6 with benzoyl chloride analogously to Example 4 gives 2-methyl-4-benzoyl-2,5-methano-2,3,4,5-tetrahydro-7-nitro-benzoxazepine (melting point 138°–140° C.).

Example 8

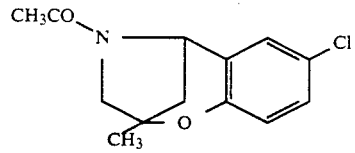

2-Methyl-4-acetyl-2,5-methano-2,3,4,5-tetrahydro-7-chlorobenzoxazepine: melting point 98°–100° C.

Example 9

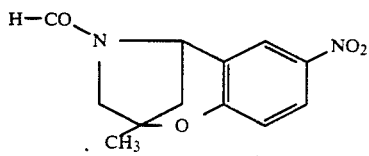

2-Methyl-4-formyl-2,5-methano-2,3,4,5-tetrahydro-7-nitrobenzoxazepine: melting point 100°–102° C.

The following benzoxazepines are obtained in an analogous manner:

TABLE 1

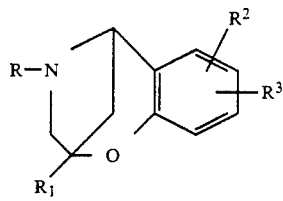

| Example No. | R | R¹ | R² | R³ | Yield % of theory | Melting point |
|---|---|---|---|---|---|---|
| 10 | CH₃CO— | CH₃ | 6-Cl | 9-CH₃ | 56 | 110° C. |
| 11 | 3-pyridyl-CO— | CH₃ | 7-NO₂ | H | 67 | 160–162° C. |
| 12 | 4-pyridyl-CO— | CH₃ | 7-NO₂ | H | 58 | 212–214° C. |
| 13 | CH₃—NH—CO— | CH₃ | 7-NO₂ | H | 93 | 189–191° C. |
| 14 | CH₃—NH—CO— | CH₃ | H | H | 69 | 168–170° C. |
| 15 | 4-Cl-C₆H₄-NH—CO— | CH₃ | H | H | 81 | 150–152° C. |

TABLE 1-continued

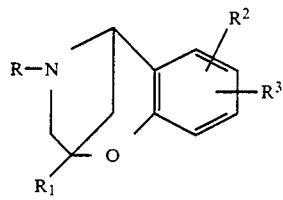

| Example No. | R | R¹ | R² | R³ | Yield % of theory | Melting point |
|---|---|---|---|---|---|---|
| 16 | $CH_3-CO-$ | $C_2H_5$ | H | H | 29 | Oil |
| 17 | $CH_3-CO-$ | $(CH_3)_2CH-CH_2-$ | H | H | 33 | Oil |
| 18 | $C_6H_5-CH_2-CO-$ | $CH_3$ | 7-$NO_2$ | H | 65 | 104–107° C. |
| 19 | $CH_3-CO-$ | $CH_3$ | 7-$CF_3O$ | H | 17 | 107–109° C. |
| 20 | $-CO-C(CH_3)_3$ | $CH_3$ | 7-$NO_2$ | H | 86 | 148–150° C. |
| 21 | $-CO-CH_2-CH-(CH_3)_2$ | $CH_3$ | 7-$NO_2$ | H | 81 | 112–114° C. |
| 22 | $-CO-CH_3$ | $CH_3$ | 7-$CF_3O$ | H | 41 | 107–9° C. |
| 23 | 3,4-di-$OCH_3$-$C_6H_3$-CO- | $CH_3$ | | H | 77 | 140–142° C. |
| 24 | $C_6H_5-CH_2-CO-$ | $CH_3$ | H | H | 74 | 86–88° C. |
| 25 | 3,4-di-$OCH_3$-$C_6H_3$-$CH_2$-CO- | $CH_3$ | H | H | 49 | Oil |
| 26 | 3,4-di-$OCH_3$-$C_6H_3$-$CH_2$-CO- | $CH_3$ | 7-$NO_2$ | H | 64 | 170–172° C. |
| 27 | $CH_3-CO$ | $CH_3$ | 6,8(di)$CH_3$ | 7-Cl | 58 | 205–207° C. |
| 28 | $CH_3-CO$ | $CH_3O$ | 6,7-Benzo- | | 61 | 118–120° C. |
| 29 | $CH_3-CO$ | $CH_3$ | 7-CN | H | 66 | 110–112° C. |
| 30 | $CH_2=CH-CH_2-NH-CS-$ | $CH_3$ | H | H | 90 | 117–119° C. |
| 31 | $CH_3-CO-$ | $CH_3$ | 8-$C_6H_5$ | H | 48 | 134–137° C. |
| 32 | $C_6H_5-SO_2-$ | $CH_3$ | 7-$NO_2$ | H | 82 | 162–164° C. |
| 33 | $CH_3-SO_2$ | $CH_3$ | H | H | 81 | 130–132° C. |
| 34 | $CH_3-CO-$ | $CH_3$ | 7-F | H | 29 | 58–60° C. |
| 35 | $CH_3-CO$ | $CH_3$ | 7-F | H | 41 | 97–98° C. |
| 36 | $CH_3-CO$ | $CH_3$ | 8-$CH_3O$ | H | 89 | 132–134° C. |
| 37 | $CH_3-CO$ | $CH_3$ | 7-$CH_3SO_2$ | H | 37 | >200° C. (Decomp.) |
| 38 | H | $CH_3$ | 7-$CF_3O$ | H | 68 | 88–90° C. |

TABLE 1-continued

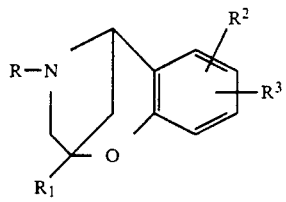

| Example No. | R | R¹ | R² | R³ | Yield % of theory | Melting point |
| --- | --- | --- | --- | --- | --- | --- |
| 39 | $CH_3$—CO | $CH_3$ | 7-$CF_3$ | H | 70 | >150° C. (Decomp.) |
| 40 | $C_2H_5$—CO | $CH_3$ | 7-$NO_2$ | H | 76 | 107–109° C. |
| 41 | phenyl-$SO_2$— | $CH_3$ | 7-$NO_2$ | H | 85 | 162–164° C. |
| 42 | phenyl-$SO_2$— | $CH_3$ | H | H | 91 | 108–110° C. |
| 43 | phenyl-$CH_2$—$CH_2$—CO— | $CH_3$ | H | H | >90 | Oil |
| 44 | 4-Cl-phenyl-NH—CO— | $CH_3$ | 7-$NO_2$ | H | 93 | 312° C. |
| 45 | pyridin-3-yl-CO— | $CH_3$ | H | H | 42 | 115–117° C. |
| 46 | $C_2H_5$—CO— | $CH_3$ | 7-$NO_2$ | H | 54 | 106–109° C. |
| 47 | $C_2H_5O$—CO— | $CH_3$ | H | H | 77 | 122–5° C. |

We claim:

1. A 2,5 methano-benzoxazepine or benzothiazepine of the formula

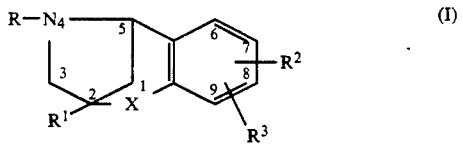

(I)

in which

X represents oxygen or sulphur,

R represents hydrogen or one of the groups $COR^4$, CO—$NHR^4$, CS—$NHR^4$, CO—$OR^4$ or $SO_2R^4$, wherein R⁴ in each case represents hydrogen, straight-chain, branched or cyclic alkyl having up to 7 C atoms, alkoxy having up to 4 C atoms, alkenyl having 2 to 4 C atoms, phenalkyl having 7 to 10 C atoms, phenyl or a 5-or 6-membered heteroaryl radical selected from the group consisting of thiophene, pyridine and furan, it being possible for the alkyl radicals mentioned to be optionally substituted by halogen and for the phenyl radicals to be optionally mono- or disubstituted by alkyl or alkoxy having in each case 1 to 4 C atoms or by halogen or nitro, R¹ represents hydrogen or alkyl having 1 to 4 C atoms and R² and R³ are identical or different and each represent a substituent selected from the group consisting of hydrogen, straight-chain, branched or cyclic alkyl having 1 to 7 C atoms, which is optionally substituted by halogen, alkoxy having 1 to 6 C atoms, halogen, nitro, carboxyl, hydroxyl, carboxamide, alkoxycarbonyl having up to 7 C atoms, alkylsulphonyl having 1 to 6 C atoms, phenylsulphonyl and a heteroaryl radical selected from the group consisting of thiophene, pyridine and furan or represent phenyl which is optionally mono- or disubstituted by alkyl or alkoxy having 1 to 4 C atoms, halogen or nitro, or represent $COR^4$, both in the form of isomer mixtures and in isomerically pure form.

2. A compound according to claim 1 in which

X represents oxygen or sulphur,

R represents hydrogen, $COR^4$, $CONHR^4$, $SCNHR^4$, CO—$OR^4$ or $SO_2R^4$, wherein R⁴ represents alkyl or alkoxy having up to 4 C atoms, it being possible for alkyl to be optionally substituted by fluorine or chlorine, or represents phenyl which is optionally mono- or disubstituted by alkyl or alkoxy having 1 to 4 C atoms, fluorine, chlorine or nitro, or represents heteroaryl from the group consisting of thiophene, pyridine and furan, which are optionally substituted by fluorine, chlorine, methyl, ethyl or methoxy, $R^1$ represents hydrogen or alkyl having 1 to 4 C atoms and $R^2$ and $R^3$ are identical or different and each represent a substituent selected from the group consisting of hydrogen, halogen, nitro, carboxyl, cyano, hydroxyl, carboxamide, phenyl, phenylsulphonyl, alkyl having 1 to 4 C atoms, alkoxy having 1 to 4 C atoms, alkoxycarbonyl having up to 5 C atoms, alkylsulphonyl having 1 to 4 C atoms, thiophene, pyridine and furan, the alkyl, aryl and heteroaryl radicals mentioned optionally being substituted by fluorine, chlorine, nitro, alkyl having 1 to 4 C atoms or alkoxy having 1 to 4 C atoms.

3. A compound according to claim 1, in which
X represents oxygen,
R represents hydrogen, $CO-R^4$, $CO-NH-R^4$, $CO-OR^4$ or $SO_2-R^4$, wherein
$R^4$ represents alkyl or alkoxy having 1 to 4 C atoms, it being possible for alkyl to be substituted by fluorine, $R^1$ represents alkyl having 1 to 4 C atoms and $R^2$ and $R^3$ are identical or different and each represent a substituent selected from the group consisting of hydrogen, halogen, nitro, cyano, alkyl having up to 4 C atoms and alkylsulphonyl having up to 4 C atoms, it being possible for the alkyl radicals mentioned to be substituted by fluorine.

4. A vaso- and muscle-relaxing composition comprising an amount effective therefor of a compound according to claim 1 and a pharmaceutically acceptable diluent.

5. A method of treating a patient afflicted with a disease of the circulatory system which comprises administering to such patient an amount effective therefor of a compound according to claim 1.

* * * * *

UNITED STATES PATENT AND TRADEMARK OFFICE
CERTIFICATE OF CORRECTION

PATENT NO. : 5,221,681

DATED : June 22, 1993

INVENTOR(S) : Kabbe, et al.

It is certified that error appears in the above-identified patent and that said Letters Patent is hereby corrected as shown below:

Col. 12, line 64   Delete " $SCNHR^4$ " and substitute -- $CSNHR^4$ --

Signed and Sealed this

Fifteenth Day of November, 1994

Attest:

BRUCE LEHMAN

*Attesting Officer*   *Commissioner of Patents and Trademarks*